(12) United States Patent
De Simone

(10) Patent No.: US 6,923,960 B2
(45) Date of Patent: Aug. 2, 2005

(54) ANTIOXIDANT COMBINATION COMPOSITION AND USE THEREOF

(75) Inventor: Claudio De Simone, Ardea (IT)

(73) Assignee: VSL Pharmaceuticals Inc., Gaithersburg, MD (US)

( * ) Notice: Subject to any disclaimer, the term of this patent is extended or adjusted under 35 U.S.C. 154(b) by 0 days.

(21) Appl. No.: 09/968,986

(22) Filed: Oct. 3, 2001

(65) Prior Publication Data

US 2003/0068309 A1 Apr. 10, 2003

(51) Int. Cl.$^7$ ................................................ A61K 47/00
(52) U.S. Cl. ...................... 424/94.1; 514/440; 514/556; 514/643; 424/451; 424/464
(58) Field of Search ................. 424/94.1, 451, 424/464, 264; 514/440, 556, 643, 436

(56) References Cited

U.S. PATENT DOCUMENTS

| | | | |
|---|---|---|---|
| 5,292,538 A | | 3/1994 | Paul et al. |
| 5,976,568 A | | 11/1999 | Riley |
| 5,998,474 A | | 12/1999 | Cavazza |
| 6,235,784 B1 | * | 5/2001 | Cavazza ...................... 514/561 |
| 6,365,622 B1 | * | 4/2002 | Cavazza ...................... 514/440 |
| 2002/0182196 A1 | * | 12/2002 | McCleary .................. 424/94.1 |

FOREIGN PATENT DOCUMENTS

| | | |
|---|---|---|
| WO | WO 98 43617 A | 10/1998 |
| WO | WO 00/00183 | 1/2000 |
| WO | WO 00/07581 | 2/2000 |
| WO | WO 00/11968 | 3/2000 |
| WO | WO 00/28986 | 5/2000 |
| WO | WO 01 21208 A | 3/2001 |
| WO | WO 01 32168 A | 5/2001 |

OTHER PUBLICATIONS

Atroshi et al, "Fumonisin B 1–induced DNA damage in rat liver and spleen: Effects of pretreatment with coenzyme Q10, selenium", Pharmacological Research, vol. 40, No. 6, Dec. 1999, pp. 459–467, XP002230270.

Mosca et al, "Modulation of apoptosis and improved redox metabolism with the use of a new antioxidant formula", Biochemical Pharmacology, vol. 63, No. 7, 2002, pp. 1305–1314, XP002230271.

* cited by examiner

*Primary Examiner*—Irene Marx
(74) *Attorney, Agent, or Firm*—Nixon & Vanderhye P.C.

(57) ABSTRACT

An orally or parenterally administrable composition which comprises the following components:
(a) L-carnitine inner salt or a pharmacologically acceptable salt thereof;
(b) acetyl L-carnitine inner salt or a pharmacologically acceptable salt thereof;
(c) α-lipoic acid;
(d) coenzyme $Q_{10}$;
(e) Vitamin E; and
(f) selenomethionine, suitable for counteracting oxidative stress and use thereof are disclosed.

1 Claim, No Drawings

ANTIOXIDANT COMBINATION COMPOSITION AND USE THEREOF

The present invention relates to a combination composition for the prevention and/or treatment of disorders or diseases brought about by oxidative stress, untimely early physiological apoptotic phenomena following oxidative stress and/or environmental agent-induced apoptosis.

Accordingly, the composition may take the form and exert the action of a dietary supplement or of an actual medicine, depending upon the support or preventive action, or strictly therapeutic action, which the composition is intended to exert in relation to the particular individuals it is to be used in.

Diseases which can effectively be prevented or treated with the composition of the present invention include atherosclerosis, ischaemia-reperfusion injuries, rheumatoid arthritis, cancer, stroke, cataract and other eye diseases, thyroid diseases, liver diseases, sexual impotence, Parkinson's disease, Alzheimer's disease and degenerative disorders affecting virus-infected patients.

Oxidative stress, untimely occurring physiological apoptotic phenomena elicited by oxidative stress and the environmental agent-induced apoptosis are brought about by reactive oxygen species; (ROS). ROS are highly reactive substances which form following physiologically normal metabolic reactions and during electron transportation in the mitochondrial respiratory chain.

Oxidative stress can be counteracted by antioxidants which are important in health maintenance through the modulation of oxidative processes taking place in the body. Oxidative damage provoked by the unregulated production of ROS has been shown as the etiological factor in a growing number of clinical disorders such as those previously listed.

Mechanisms responsible for the ROS-mediated injury to cells and tissues mainly include lipid peroxidation, oxidative DNA damage, and protein oxidation, but there is also evidence that ROS can induce the procedure of cell death. Indeed, imbalance in the endogenous antioxidant system can modulate cellular proliferation, either in a positive or a negative way, respectively leading to a stimulation in cell proliferation at low levels of peroxides or to apoptotic/necrotic cell death at higher concentrations.

It is therefore apparent that investigating compounds able to counteract this oxidative stress may have a relevant clinical impact. Balanced human diets contain multiple antioxidants and there is strong evidence that additive and synergistic interactions occur among those antioxidant substances. Under a clinical perspective, this suggests that the use of combination compositions containing multiple substances with antioxidant properties have the potential to provide a significantly better protection against oxidative stress than the use of each single antioxidant alone.

The main object of the present invention is to provide such a combination composition.

It has now been found that an orally or parenterally administrable composition (i) which comprises in administrative or separately packaged form the following components:
(a) L-carnitine inner salt or a pharmacologically acceptable salt thereof;
(b) acetyl L-carnitine inner salt or a pharmacologically acceptable salt thereof;
(c) α-lipoic acid;
(d) coenzyme $Q_{10}$;
(e) Vitamin E; and
(f) selenomethionine, fully accomplishes the sought-after aim of potently counteracting oxidative stress.

What is meant by a pharmacologically acceptable salt of L-carnitine and acetyl L-carnitine is any salt of these with an acid which does not give rise to unwanted toxic or side effects. These acids are well known to pharmacologists and to experts in pharmaceutical technology.

Non limiting examples of such salts are the following: chloride; bromide; iodide; aspartate, acid aspartate; citrate, acid citrate; tartrate; phosphate, acid phosphate; fumarate, acid fumarate; galactarate; glycerophosphate; glucose phosphate; lactate; maleate, acid maleate; orotate; oxalate; acid oxalate; sulphate, acid sulphate; trichloroacetate; trifluoroacetate and methane sulphonate A list of FDA-approved pharmacologically acceptable acids is given in *Int. J. Pharm.*, 33, 1986, 201–217, the latter publication being incorporated in the present description for reference purposes.

For the preparation of solid administration forms, such as, for example, tablets, pills, capsules and granulates, the use of non-hygroscopic salts is preferred.

The composition of the present invention in unit dosage form (ii) comprises:
(a) 20–110 mg L-carnitine inner salt or an equivalent molar amount of a pharmacologically acceptable salt thereof;
(b) 20–110 mg acetyl L-carnitine inner salt or an equivalent molar amount of a pharmacologically acceptable salt thereof;
(c) 70–130 mg α-lipoic acid;
(d) 90–110 mg coenzyme $Q_{10}$;
(e) 5–15 mg Vitamin E; and
(f) 40–60 μg selenomethionine.

A particularly preferred composition (iii) comprises:
(a) 100 mg L-carnitine inner salt;
(b) 100 mg acetyl L-carnitine inner salt;
(c) 100 mg α-lipoic acid;
(d) 100 mg coenzyme $Q_{10}$;
(e) 10 mg Vitamin E; and
(f) 50 μg selenomethionine.

The present invention also relates to a prevention/therapeutical method which comprises administering a patient in need thereof an effective amount of the aforesaid composition (i). Patients who are staying on a multiple dose administration regimen are preferably administered in unit dosage form (ii) and, more particularly, the unit dosage form (iii). The present method is particularly suited for patients receiving arginine supplementation since these compositions are particularly effective for preventing/counteracting NO-induced oxidative damages elicited by arginine supplementation.

During the last few years, diet supplements comprising arginine have become more and more recommended not only by nutritionally oriented physicians but also by cardiologists and endocrinologists Arginine decreases cholesterol more effectively than any other amino acid. Daily doses of 6–17 grams of arginine have been shown to lower LDL-cholesterol without affecting HDL-cholesterol nor eliciting side effects. Arginine also promotes healthy coronary microcirculation in people with high cholesterol and inhibits the formation of blood clots, a main etiological factor leading to heart attacks and strokes. Infusion of arginine directly into the coronary blood vessels of angina patients was reported to dramatically restore their circulation.

Arginine is an NO-precursor. Nitrogen oxide (NO) is produced normally by many cell types and plays several roles ranging from neurotransmission to vasodilatation. By relaxing arteries NO can improve circulation-related conditions such as angina, intermittent claudication, high blood pressure and impaired brain circulation.

Despite all its benefit, NO is a free radical, toxic oxidant: pulmonary toxicity can occur with levels over 50 to 100 ppm.

Clinical Trial

The antioxidant efficacy of the composition previously indicated a (iii) was assessed in the following clinical trial. The presentation form of the composition was as sachets.

1.1 Study Design

The trial was a 16-week randomized trial. A total of 20 healthy subjects (12 men, 8 women) were enrolled in the study. The subjects had to fulfil the following inclusion criteria: non-smokers, not taking vitamin/antioxidant or estrogen supplements, thyroxin, or lipid-lowering drugs; normal plasma glucose, hepatic and renal function tests; no acute medical conditions at least three months prior to entry into the study. Participants were advised to not adopt any particular lifestyle, to adhere to their usual diet and physical activity during the course of the experiments and not to vary their consumption of vitamin rich foods; none were taking any additional supplements or medications during the study period. Participants gave written informed consent and were requested to report on compliance on a weekly basis.

Participants were assigned to receive antioxidant supplements in the form of 1 sachet of composition (iii) per day over a 3-week period. The sachet was taken daily in the morning after meals. Control group A (5 subjects) received only acetyl L-carnitine and L-carnitine and control group B (6 subjects) was given only selenomethionine, α-tocopherol, α-lipoic acid and coenzyme $Q_{10}$ in the same amounts as those of composition (iii).

Subjects enrolled in the study group and subjects in both control groups were similar with respect to age, body mass-index, and lipid profile at entry into the study. Safety assessments included the evaluation of adverse events and vital signs, hematologic tests, biochemical tests, urine analysis, and physical examination. These assessments were done at base-line before treatment was started and, then, at weekly intervals during the treatment period and two weeks after completion of the study.

1.2 Assay of Antioxidant Enzymes

Enzyme activities were determined in fresh erythrocytes. After centrifugation of 1 ml blood, the erythrocytes were washed three times with isotonic solution and then lysed in bidistilled water (final volume 5 ml). Superoxide dismutase (SOD) activity was determined according to Flohé and Otting (Flohé, L., Otting F., *Methods Enzymol.* 105:93–104, 1984). Catalase (CAT) activity was determined according to Pippenger et al [Pippenger, C. E., Browne, R. W., Armstrong, D., Regulatory antioxidant enzymes; Methods in Molecular Biology; Free Radical and Antioxidant Protocols (D. Armstrong, Ed.) vol 108, pp 299–313, Humana Press, Totowa N.J., 1998.]. Glutathione peroxidase (GSHPX) activity was determined according to Flohé and Gunzler (Flohé, L., Gunzler, W. A., *Methods Enzymol.* 105:114–121, 1984). Results are expressed as Enzyme Units/mg Hemoglobin.

1.3 Plasma Vitamin E, Coenzyme $Q_{10}$ and $QH_2$ Measurement

Vitamin E and coenzyme $Q_{10}$ determinations were performed by the procedure of Lang et al (Lang, J. K., Gohil, K., Packer, L., *Anal. Biochem.* 157:106–116, 1986). Plasma was obtained from freshly drawn heparinised venous blood by brief centrifugation (800 g for 5 min at 4° C.). 1 ml plasma was mixed with 1 ml ethanol containing 0.1 mM BHT and extracted with 3 ml hexane. The hexane phase was then evaporated to dryness under nitrogen stream and re-dissolved in ethanol. 400 µl was filtered onto 0.45 µm filters and then an aliquot of 100 µl was analysed by HPLC. The HPLC system consisted of a Waters apparatus, equipped with two 510 pumps, a Rheodyne injection valve with a 100 µl loop, a Symmetry 300 column (C18 reverse phase, 4.6×25 cm, 5 µm particle size), thermostated at 27° C. with a guard column (10 mm) of the same material matrix, a Waters 996 Diode array detector and a Waters 474 spectrofluorometer detector. The two detectors were set up in line, the column effluent first passing through the UV detector. The elution was performed at a flow rate of 1 ml/min with a gradient consisting of a mixture of A (80/20 v/v methanol/$H_2O$) and B (95/5 v/v ethanol/isopropanol). The initial conditions were 39% A and 61% B. After 16 min the mobile phase was changed linearly over 2 min to 100% B; 100% B continued for 10 min, after which the system reversed linearly over 2 min to the initial conditions. Peak identification was performed on the basis of the retention time and of the absorption spectrum for ubiquinol (Rt=25.1 min; λmax=290 nm) and ubiquinone (Rt=27.1 min; λmax=275 nm), and retention time, absorption spectrum and fluorescence for vitamin E (Rt=18.2 min; λmax=292 nm; λex=220 nm, λem=335 nm). Peak quantitation was performed by automatic peak area integration using a dedicated software. Results are expressed as nmoles/ml plasma.

1.4 TRAP Assay

Total radical-trapping antioxidant parameter (TRAP) was determined according to Ghiselli et al (Ghiselli, A., Serafini, M., Maiani G., Azzini, E., Ferro-Luzzi, A., *Free Radic. Biol. Med.* 18:29–36, 1995.

1.5 Plasma Hydroperoxides Quantitation

The assessment of the oxidising capacity in blood serum was carried out using the D-ROMs kit test produced by DIACRON s.r.l., Italy. The method is based upon the capacity of transition metals to catalyse the formation of hydroxyl radicals (—OH) in the presence of hydroperoxides by Fenton-type reactions. The —OH produced, whose quantity is directly proportional to the amount of peroxides present in plasma, were trapped by molecules of N,N-diethyl-p-phenylene diamine, with the formation of a chromogen with a λmax at 505 nm.

1.6 Lymphocyte Isolation

PBMCs were separated from heparinised peripheral blood by Lymphoprep gradient centrifugation (Nycomed, Oslo, Norway), washed twice with phosphate buffered saline (PBS) and resuspended in RPMI 1640 (Life Technologics, Inc., Paisley, UK) medium supplemented with 10% heat-inactivated fetal calf serum (FCS; Life Technologics), 10 IU/ml penicillin/streptomycin (Life Technologics), 10 mM HEPES (Sigma Chemical Company, St. Louis, Mo., USA), and 1 mM L-glutamine (Life Technologics) (complete medium). In the apoptosis assay, PBMCs ($5 \times 10^5$/ml) were cultured in complete medium for 12 hours at 37° C. in a 5% $CO_2$-humidified atmosphere. In addition, for the analysis of mitochondrial functions, aliquots of cells were isolated and maintained in complete culture medium at 4° C. until labeling.

1.7 Expression of Surface and Intracellular Antigens

The absolute counts of cells bearing either the CD4 or the CD8 phenotype were determined by flow cytometry. PBMCs were stained with the following antibodies: phycoerythrine (PE)-labeled anti-hCD4 or anti-hCD8 (Becton Dickinson, Immunocytometry Systems, BDIS, San José, Calif., USA). For staining of surface antigens $5 \times 10^5$ PBMCs were washed in PBS containing 1% BSA (Sigma) and 0,1% sodium azide (PBS-BSA-$NaN_3$) followed by incubation for 20 minutes at 4° C. with the mAbs previously described. For determination of background staining, cells were incubated with 20 µl of mouse IgG1 PE (Becton Dickinson). Then, after 2 washing with PBS-BSA-NaN$_3$ containing 2% FCS, the labelled cells were analysed by flow cytometry using a FACScan flow cytometer (Becton Dickinson). For each sample 10,000 viable lymphocytes were gated, following size (forward scatter, FSC) and granularity (side scatter, SSC) parameters.

1.8 Staining of Apoptotic Nuclei with Propidium Iodide (PI)

Lymphocyte apoptosis was quantified as the percentage of cells with hypodiploid DNA using the technique of Nicoletti et al (Nicoletti, I.; Migliorati, G.; Pagliacci, C.; Grignani, F.; Riccardi, C., *J. Immunol. Methods* 139:271–279, 1968). Briefly, following a short term culture, cell suspensions were centrifuged at 200 g for 10 minutes. For staining of surface antigens, aliquots of 1×10$^6$ cells were incubated with fluorescein isothiocyanate (FITC)-conjugated anti-hCD4 or anti-hCD8 (Becton Dickinson) mAbs as previously described and, after washing, the pellet was gently re-suspended in 1 ml of hypotonic fluorochrome solution (50 µg/ml PI in 0.1% sodium citrate plus 0.1% Triton X-100™, 0.05 mg/ml RNase A; Sigma). Cells were kept overnight at 4° C., then analysed in their staining solution on a FACScan flow cytometer (Becton Dickinson) equipped with a 15 mW air-cooled 488 nm argon-ion laser. Apoptotic nuclei appeared as a broad hypodiploid DNA peak which was easily discriminable from the narrow peak of nuclei with normal (diploid) DNA content in the red fluorescence channel. Orange PI fluorescence was collected after a 585/42 nm band pass filter and was displayed on a four-decade log scale. Acquisition on the flow cytometer was done in the low sample flow rate setting (12 µl/min) to improve the coefficient of variation on the DNA histograms. Lymphocytes, including live, early apoptotic and late apoptotic cells, were gated on the basis of their FSC and SSC parameters, and fluorescence data were gated on FSC vs. PI fluorescence dual-parameter contour plots for exclusion of monocytes, debris and clumps. This method of gating allowed ready discrimination of debris (very low FSC and decreased PI fluorescence) from dead cells (low FSC and high PI fluorescence). A minimum of 10,000 events was collected on each sample.

1.9 Phenotypic Analysis of Apoptotic T Cells

Quantification and phenotypic analysis of apoptotic cells from the short term cultured lymphocytes was performed by staining apoptotic cells with 7-amino-actinomycin D (7-AAD; Sigma) as reported by Schmid et al (Schmid, I., Uittenbogaart, C. H., Keld, B., Giorgi, J. V., *J. Immunol. Methods* 170:145–157; 1994). This method was shown to discriminate between early and late apoptotic cells due to their increased membrane permeability. Cultured lymphocytes were first incubated with FITC-conjugated mAbs to surface Ags as described above, and washed cells were then incubated with 20 µg/ml of 7-AAD for 20 minutes at 4° C. protected from light. Stained cells were further fixed with 1% paraformaldehyde in PBS in the presence of 20 µg/ml of non-fluorescent actinomycin D (Sigma) to block 7-AAD staining within apoptotic cells and avoid non-specific labeling of living cells. Finally, the double-stained cells were incubated overnight at 4° C. in the dark and were then analysed in their staining solution by a FACScan flow cytometer (Becton Dickinson). The green fluorescence was collected after a 530/30 BP nm filter, the red fluorescence from 7-AAD was filtered through a 650 long pass filter. Scattergrams were generated by combining FSC with 7-AAD fluorescence, and regions were drawn around clear-cut populations having negative (live cells), dim (early apoptotic cells), and bright fluorescence (late apoptotic cells). A minimum of 10,000 events was collected on each sample.

1.10 Analysis of Mitochondrial Functions

For the simultaneous assessment of surface markers and ROS generation, such as superoxide anion and hydroxyperoxides, cells were first stained with PE-labeled anti-hCD4 or anti-hCD8 antibodies and then exposed for 15 minutes at 37° C. to 2 mmol/l hydroethidine (HE; Molecular Probes) and for 1 hour at 37° C. to 5 mM 2',7'-dichlorofluorescein diacetate (DCFH-DA) (Molecular Probes) respectively. In control experiments, cells were labelled after pre-incubation with the uncoupling agent carbonyl cyanide m-chlorophenyl-hydrazone (mClCCP; 50 mmol/l, 37° C., 30 minutes; Sigma), or the ROS-generating agent menadione (1 mmol/l, 37° C., 1 hour, Sigma). For DCFH-DA, a positive control (cells kept 2 minutes in 15 mM H$_2$O$_2$ and washed three times) was inserted. Monobromobimane (MBB) (Molecular Probes) stains glutathione (GSH). In the presence of glutathione-S-transferase, MBB combines not enzymatically with GSH at low concentrations, resulting in GSH-specific fluorescence. Briefly, T cells were pelleted and resuspended in 1 ml medium containing 40 µM MBB for 10 minutes at room temperature in the dark. Cells were placed on ice before analysis performed on a FACScan cytofluorometer (Becton Dickinson). FSC and SSC parameters were gated on the major population of normal-sized lymphoid cells. After suitable compensation, fluorescence was recorded at different wavelengths: FITC, DCFH-DA and MBB at 525 nm (FL-1), PE at 575 nm (FL-2) and HE at 600 nm (FL-3).

2 Statistical Analysis

All the results are expressed as the mean values±standard deviation. Statistical comparison between groups was made using Student's t test. p values<0.05 were regarded as significant.

Results

Plasma Antioxidant Status and Peroxide Levels

Supplementation with the aforesaid composition (iii) for 21 days resulted in a significant increase in the total antioxidant status (Table 1). Supportive evidence for this improved antioxidant status was obtained by measurement of TRAP values and lipid peroxidation products in blood plasma. A comparable increase in TRAP values was also observed in the two control groups who were given only some of the composition components, respectively carnitines in control group A and selenomethionine, α-tocopherol, α-lipoic acid and coenzyme Q$_{10}$ in control group B. Conversely, plasma peroxide levels were found significantly lowered at the end of the treatment compared to the base-line in the composition group and in both control groups to a lower extent.

Base-line plasma levels for vitamin E, coenzyme Q$_{10}$ and QH$_2$ were 26, 0.50, and 0.66 nmol/ml, respectively, which are comparable to data reported in the literature. Supplementation with the composition for 3 weeks resulted into an increase in mean plasma levels of alpha-tocopherol, coenzyme Q$_{10}$, QH$_2$, and in QH$_2$/(Q$_{10}$+QH$_2$) ratio (Table 1). It is of interest that supplementation with the composition resulted in a 1.5 fold increment of the plasma coenzyme concentration, mainly in its reduced form.

Activity of Antioxidant Enzymes in Red Blood Cells

In the treatment group, administration of the composition resulted in a significant increase in the specific activity of the antioxidant enzyme GSHPX (p<0.01) at the end of the treatment period compared with base-line values (Table 2). A comparable increase in GSHPX activity was also found in control group B (p<0.01). No significant change in SOD activity was found after supplementation either with the composition or with some components of the composition. CAT activity was significantly decreased at the end of the study period in the group given the composition as compared to base-line (p<0.05); a trend towards a reduction in CAT activity was observed also in both control groups but the difference with values measured before administering some of the composition components did not reach the statistical significance.

Lymphocyte Apoptosis

Supplementation with the composition was associated with a reduced susceptibility of lymphocytes to apoptosis. In fact, a lower number of lymphocytes was undergoing apoptosis in treated patients after 3 weeks of supplementation as compared to base-line. This was established by staining apoptotic nuclei with PI (see Nicoletti et al, supra), which detects late events of apoptosis such as chromatin condensation and DNA fragmentation (Wyllie, A. N., Morris, R. G.; Smith, A. L.; Dunlop, D., *J. Pathol.* 142:67–77; 1991. Following 12 hours of incubation in complete medium, the rate of spontaneous apoptosis was significantly decreased in CD4 and CD8 lymphocytes taken after 3 weeks of treatment as compared with pre-treatment levels (6.1±2.59 and 6.8±3.03 at base-line, 2.8±1.52 and 3.9±2.09 at the end of the treatment, respectively for CD4 and CD8 cells; p<0.01 for both parameters) (Table 3). Supplementation with carnitines only had a comparable, and even greater, impact on the frequency of CD4 and CD8 lymphocytes undergoing apoptosis (7.2+1.19 and 12.2+3.24 at base-line, 3.9+1.19 and 5.4+1.94 at the end of the treatment, respectively for CD4 and CD8 lymphocytes; p<0.01 both for CD4 and CD8 cells). Even subjects who were given selenomethionine, α-tocopherol, α-lipoic acid, and coenzyme $Q_{10}$ had a strong decrease in the frequency of apoptotic lymphocytes compared to pre-treatment levels (6.7+1.58 and 8.6 +1.91 at base-line, 3.7 +1.59 and 5.9 +1.12 at the end of the treatment, respectively for CD4 and CD8 cells, p<0.01 for both parameters).

These results were confirmed by measuring apoptosis also with 7-AAD, a fluorescent DNA-intercalating agent which only penetrates the membrane of cells undergoing apoptosis and thus exhibit a shrunked phenotype (reduced FSC) (p<0.001 for both parameters) (Table 3).

Generation of Reactive Oxygen Species

As shown in Table 4, circulating lymphocytes from the healthy volunteers enrolled in this study contained a fraction of cells which were able to oxidize the nonfluorescent lipophilic (i.e., membrane-permeable) dye HE into the hydrophilic fluorescent product Eth. Since HE is particularly sensitive to superoxide anion, this change is thought to reflect the generation of superoxide anion (Rothe, G.; Valet, G., *J. Leukoc. Biol.* 47:440–446, 1990). Moreover, lymphocytes were labeled using DCFH-DA, a fluorochrome that detects hydroperoxide generation (Rothe et al, supra, and Hockenbery, D. M., Oltvai, Z. N., Yin, X. M., Milliman, C. L., Korsmeyer, S. J., *Cell* 75:241–251, 1993.

Supplementation with the composition was found to be associated with a strong decrease in the percentage of such cells, which bear an $Eth^{high}$ and DCFH-DA-positive phenotype, as compared to pre-treatment levels (Table 4). Statistical analysis revealed a highly significant difference between pre- and post-treatment levels with respect to CD4 and CD8 cells stained with either HE or DCFH-DA (p<0.001 for both parameters).

A significant reduction in the frequency of $Eth^{high}$ and DCFH-DA-positive CD4 and CD8 subset was found also in the control groups A and B even though the impact of supplementation on those parameters, although statistically significant, was less striking as compared to the treatment with the composition (Table 4).

The treatment with the composition was also associated with an increased frequency of circulating lymphocytes with either CD4 or CD8 surface phenotype that stained positive for glutathione (CD4: 55.1±7.71 and 59.2±4.58; CD8: 69.4±4.98 and 74.9±6.29, at T0 and T1, respectively, p<0.05 and <0.01, respectively). We observed a similar trend even in subjects given only acetyl-L-carnitine and L-carnitine (CD4: 56.9±4.58 and 61.1±3.49; CD8: 64.9±7.22 and 76.3±6.77, at T0 and T1, respectively, p<0.18 and <0.05, respectively), or the components of the composition alone, i.e. selenomethionine, α-lipoic acid, α-tocopherol, and coenzyme $Q_{10}$ (CD4: 51.6±3.72 and 60.3±1.91; CD8: 63.7±5.87 and 72.5±4.30, at T0 and T1, respectively, p<0.01 and <0.05, respectively).

Safety Profile

Treatment with the composition was well tolerated and none of the subjects enrolled experienced adverse effects. No abnormalities were detected via hematologic and biochemical tests.

TABLE 1

Plasma antioxidant status

| | Composition (iii) | | Control A | |
|---|---|---|---|---|
| | Control B | | | |
| | Before | After | Before | After |
| | Before | After | | |
| Vitamin E (nmol/ml) | 25.61 ± 5.38 | 28.81 ± 6.89* | 25.82 ± 6.25 | 26.78 ± 6.86 |
| | 22.56 ± 3.71 | 23.37 ± 3.37 | | |
| $QH_2$ (nmol/ml) | 0.462 ± 0.117 | 0.784 ± 0.259 | 0.338 ± 0.116 | 0.229 ± 0.148 |
| | 0.428 ± 0.058 | 0.441 ± 0.124 | | |
| $Q_{10}$ tot (nmol/ml) | 0.969 ± 0.266 | 1.414 ± 0.591* | 1.017 ± 0.220 | 1.353 ± 0.492 |
| | 0.910 ± 0.160 | 1.042 ± 0.335* | | |
| TRAP (trolox eq./L) | 1510 ± 270 | 1631 ± 306* | 1602 ± 200 | 1654 ± 145 |
| | 1582 ± 141 | 1536 ± 272 | | |
| LOOH (U. Carr.) | 301 ± 73 | 272 ± 51* | 327 ± 38 | 292 ± 51 |
| | 263 ± 41 | 259 ± 55 | | |

*p < 0.05
**p < 0.01
***p < 0.001

TABLE 2

Antioxidant enzymes activity

| | Composition (iii) Control B | | Control A | |
|---|---|---|---|---|
| | Before | After | Before | After |
| | Before | After | | |
| CAT (U/mg Hb) | 22.54 ± 3.19 | 15.60 ± 1.63** | 25.34 ± 1.91 | 24.53 ± 3.04 |
| | 22.50 ± 3.87 | 20.87 ± 1.80 | | |
| SOD (U/mg Hb) | 5.54 ± 1.36 | 7.63 ± 3.10 | 5.78 ± 2.61 | 6.43 ± 2.11 |
| | 5.75 ± 1.89 | 7.37 ± 1.55 | | |
| GSHPx (U/mg Hb) | 0.036 ± 0.011 | 0.046 ± 0.007** | 0.033 ± 0.02 | 0.037 ± 0.014 |
| | 0.032 ± 0.018 | 0.038 ± 0.017** | | |

*$p < 0.05$
**$p < 0.01$
***$p < 0.001$

TABLE 3

Staining for apoptotic lymphocytes

| | | Composition (iii) | | Control A | Control B |
|---|---|---|---|---|---|
| | | Before | After | Before | After |
| | | Before | After | | |
| PI staining | CD4 | | 2.81 ± 1.52*** | 7.23 ± 1.19 | 3.89 ± 1.19** |
| | | 6.11 ± 2.59 | | | |
| | | 6.69 ± 1.58 | 3.73 ± 1.59* | 12.19 ± 3.24 | 5.35 ± 1.94** |
| | CD8 | | 3.94 ± 2.09** | | |
| | | 6.81 ± 3.03 | | | |
| | | 8.60 ± 1.91 | 5.86 ± 1.12* | | |
| 7-AAD staining | CD4 | | 2.78 ± 1.51*** | 7.23 ± 1.13 | 3.89 ± 1.14** |
| | | 6.14 ± 2.60 | | | |
| | | 6.73 ± 1.65 | 3.75 ± 1.55* | 12.18 ± 3.23 | 5.40 ± 1.88** |
| | CD8 | | 3.92 ± 2.06** | | |
| | | 6.81 ± 3.05 | | | |
| | | 8.61 ± 1.97 | 5.87 ± 0.98* | | |

*$p < 0.05$
**$p < 0.01$
***$p < 0.001$

TABLE 4

Staining for reactive oxygen species at the mitochondrial level

| | | Composition (iii) | | Control A | Control B |
|---|---|---|---|---|---|
| | | Before | After | Before | After |
| | | Before | After | | |
| HE staining | CD4 | | 3.06 ± 0.95*** | 14.19 ± 5.35 | 5.06 ± 1.21** |
| | | 9.98 ± 3.22 | | | |
| | | 10.36 ± 4.80 | 5.14 ± 1.43 | | |
| | CD8 | | 4.48 ± 1.72*** | 19.88 ± 6.11 | 9.76 ± 4.88* |
| | | 17.20 ± 4.82 | | | |
| | | 13.37 ± 3.88 | 6.43 ± 1.07** | | |
| DCFH staining | CD4 | | 8.34 ± 2.28*** | 13.22 ± 2.34 | 9.89 ± 2.30 |
| | | 13.42 ± 3.02 | | | |
| | | 14.19 ± 2.85 | 9.20 ± 1.37** | | |
| | CD8 | | 8.78 ± 3.63** | 19.22 ± 5.81 | 13.18 ± 4.34 |
| | | 14.59 ± 6.57 | | | |
| | | 21.15 ± 6.09 | 14.23 ± 3.56 | | |
| MBB staining | CD4 | | 59.18 ± 4.58* | 56.92 ± 4.58 | 61.07 ± 3.49 |
| | | 55.13 ± 7.71 | | | |
| | | 51.61 ± 3.72 | 60.28 ± 1.91* | | |
| | CD8 | | 74.91 ± 6.29** | 64.87 ± 7.22 | 76.30 ± 6.77 |
| | | 69.37 ± 4.98 | | | |
| | | 63.70 ± 5.87 | 72.51 ± 4.30* | | |

*$p < 0.05$
**$p < 0.01$
***$p < 0.001$

ABBREVIATIONS

| | |
|---|---|
| 7-AAD | 7-amino-actinomycin D |
| ABAP | 2.2'-Azobis(2-amidinopropane) |
| CAT | catalase |
| DCFH-DA | 2',7'-dichlorofluorescein diacetate |
| DPPH | 1,1-diphenyl-2-picryl-hydrazil |
| FITC | fluorescein isothiocyanate |
| FSC | forward scatter |
| GSH | glutathione |
| GSHPX | glutathione peroxidase |
| HE | hydroethidine |
| MBB | monobromobimane |
| mClCCP | carbonyl cyanide m-chlorophenyl-hydrazone |
| .OH | hydroxyl radical |
| PBMCs | peripheral blood mononuclear cells |
| PBS | phosphate buffered saline |
| PI | propidium iodide |
| Q10 | coenzyme $Q_{10}$ oxidized form ubiquinone |
| QH2 | coenzyme $Q_{10}$ reduced form ubiquinol |
| R-PE | R-phycoerythrin |
| ROS | reactive oxygen species |
| SOD | superoxide dismutase |
| SSC | side scatter |
| TBARS | thiobarbituric acid reacting substances |
| TRAP | total radical-trapping antioxidant parameter |
| LOOH | lipid peroxides |

What is claimed is:

1. A therapeutic method for counteracting nitrogen oxide-induced oxidative stress in patients receiving arginine supplementation which comprises administering to a patient in need thereof an effective amount of a combination composition consisting essentially of:
   (a) 20–110 mg L-carnitine inner salt or a pharmacologically acceptable salt thereof,
   (b) 20–110 mg acetyl L-carnitine inner salt or a pharmacologically acceptable salt thereof,
   (c) 70–130 mg α-lipoic acid;
   (d) 90–110 mg coenzyme $Q_{10}$;
   (e) 5–15 mg Vitamin E; and
   (f) 40–60 μm selenomethionine.

* * * * *